United States Patent
Eroglu et al.

(10) Patent No.: US 11,660,038 B2
(45) Date of Patent: May 30, 2023

(54) SYSTEM BASED ON MULTI-SENSORY LEARNING AND EEG BIOFEEDBACK FOR IMPROVING READING ABILITY

(71) Applicant: SABANCI UNIVERSITESI, Istanbul (TR)

(72) Inventors: Gunet Eroglu, Istanbul (TR); Mujdat Cetin, Istanbul (TR); Selim Balcisoy, Istanbul (TR)

(73) Assignee: SABANCI UNIVERSITESI, Istanbul (TR)

( * ) Notice: Subject to any disclaimer, the term of this patent is extended or adjusted under 35 U.S.C. 154(b) by 410 days.

(21) Appl. No.: 16/652,440

(22) PCT Filed: Nov. 16, 2017

(86) PCT No.: PCT/TR2017/050572
§ 371 (c)(1),
(2) Date: Mar. 31, 2020

(87) PCT Pub. No.: WO2019/098951
PCT Pub. Date: May 23, 2019

(65) Prior Publication Data
US 2020/0281495 A1 Sep. 10, 2020

(51) Int. Cl.
*A61B 5/375* (2021.01)
*A61B 5/38* (2021.01)
(Continued)

(52) U.S. Cl.
CPC .............. *A61B 5/375* (2021.01); *A61B 5/291* (2021.01); *A61B 5/378* (2021.01); *A61B 5/38* (2021.01); *A61B 5/6803* (2013.01); *G06F 3/015* (2013.01)

(58) Field of Classification Search
CPC .......... A61B 5/291; A61B 5/375; A61B 5/378; A61B 5/38; A61B 5/4088; A61B 5/4836;
(Continued)

(56) References Cited

U.S. PATENT DOCUMENTS 8,082,031 B2   12/2011   Ochs
8,239,014 B2   8/2012   Ochs
(Continued)

FOREIGN PATENT DOCUMENTS

EP   1304073 A2   4/2003
WO   WO-2016182974 A1 * 11/2016   ............... A61B 5/00

OTHER PUBLICATIONS

Howard, D., Patterson, K., Wise, R., Brown, W. D., Friston, K., Weiller, C., & Frackowalk, R. (1992). The cortical localization of the lexicons. Brain, 115(6), 1769-1782. https://doi.org/10.1093/brain/115.6.1769 (Year: 1992).*
(Continued)

*Primary Examiner* — Thaddeus B Cox
*Assistant Examiner* — Marc D. Honrath
(74) *Attorney, Agent, or Firm* — Bayramoglu Law Offices LLC

(57) ABSTRACT

A system and method for improving reading ability simultaneously utilizing a distinctive protocol of multi-sensory learning and EEG biofeedback. The present invention more particularly relates to an EEG biofeedback system comprising a biofeedback apparatus in the form of a head-mountable device including an electrode array for measuring bioelectrical signals generated by a cerebral cortex of a user's brain and a computer device receiving and analyzing data collected by said biofeedback apparatus and providing audiovisual feedback to the user.

4 Claims, 3 Drawing Sheets

(51) Int. Cl.
 *A61B 5/291* (2021.01)
 *A61B 5/378* (2021.01)
 *A61B 5/00* (2006.01)
 *G06F 3/01* (2006.01)

(58) Field of Classification Search
 CPC ... A61B 5/6803; A61M 2230/10; G06F 3/015
 See application file for complete search history.

(56) References Cited

U.S. PATENT DOCUMENTS

| | | |
|---|---|---|
| 2010/0016753 A1 | 1/2010 | Firlik |
| 2010/0094156 A1 | 4/2010 | Collura |
| 2014/0200432 A1 | 7/2014 | Banerji et al. |
| 2016/0196765 A1 | 7/2016 | Stauch et al. |

OTHER PUBLICATIONS

Breteler, M. H., Arns, M., Peters, S., Giepmans, I., & Verhoeven, L. (2009). Improvements in spelling after QEEG-based neurofeedback in dyslexia: A randomized controlled treatment study. Applied Psychophysiology and Biofeedback, 35(1), 5-11. https://doi.org/10.1007/s10484-009-9105-2 (Year: 2009).*

Nazari, M. A., Mosanezhad, E., Hashemi, T., & Jahan, A. (2012). The effectiveness of neurofeedback training on EEG coherence and neuropsychological functions in children with reading disability. Clinical EEG and Neuroscience, 43(4), 315-322. https://doi.org/10.1177/1550059412451880 (Year: 2012).*

BrainMaster Technologies. (Oct. 15, 2014). Electrode Positions. Neurofeedback, qEEG, biofeedback, and more—BrainMaster Tech Inc.. Retrieved May 4, 2022, from https://web.archive.org/web/20141015041718/http://www.brainm.com/software/pubs/dg/BA_10-20_ROI_Talairach/nearesteeg.htm (Year: 2014).*

Raesi, S., Dadgar, H., Soleymani, Z., & Hajjeforoush, V. (2017). Efficacy of neurofeedback training on reading and spelling skills of 8 to 12 years old children with dyslexia. Journal of Modern Rehabilitation, 10(4), 177-184. https://doi.org/10.18869/nirp.jmr.10.4.177 (Year: 2017).*

Nunez, P. L., & Srinivasan, R. (Feb. 4, 2007). "Electroencephalogram". Scholarpedia. Retrieved May 5, 2022, from http://www.scholarpedia.org/article/Electroencephalogram (Year: 2007).*

BrainMasterTechnologies. (Oct. 15, 2014). Electrode Positions. Neurofeedback, qEEG, biofeedback, and more—BrainMaster u Tech Inc .. Retrieved May 4, 2022, from https://web.archive.org/web/20141015041718/http://www.brainm.com/software/pubs/dg/BA_10-20_ROI_Talairach/nearesteeg.htm (Year: 2014).*

Ramirez, R., Palencia-Lefler, M., Giraldo, S., ; Vamvakousis, Z. (2015). Musical neurofeedback for treating depression in elderly people. Frontiers in Neuroscience, 9. https://doi.org/10.3389/fnins.2015.00354 (Year: 2015).*

G. Reid Lyon, et al., A Definition of Dyslexia, Defining Dyslexia, Comorbidity, Teachers' Knowledge of Language and Reading, 2003, pp. 1-14, vol. 53.

Martijn Arns, et al., Different brain activation patterns in dyslexic children: Evidence from EEG power and coherence patterns for the double-deficit theory of dyslexia, Journal of Integrative Neuroscience, 2007, pp. 175-190, vol. 6.

T. Fernandez, et al., EEG and Behavioral Changes Following NeurofeedbackTreatment in Learning Disabled Children, Clinical Electroencephalography, 2003, pp. 145-152, vol. 34.

Manuel Ninaus, et al., Neurofeedback and Serious Games, Connolly, TM, Hainey, T., Boyle, E., Baxter, G., Moreno-Ger, P.(eds.), 2013, pp. 82-110.

Alyssa Ashbaugh, "Multi-Sensory Techniques in Spelling Instruction: An Action Research Study for Students with Dyslexia." 2016,pp. 1-85.

Eraldo Paulesu, et al., Dyslexia as a disconnection syndrome. Brain, 1996, pp. 143-157, vol. 119.

George H. Klem, et al. The ten-twenty electrode system of the International Federation, International Federation of Clinical Neurophysiology, 1999, pp. 3-6, vol. 52, Elsevier Science B.V.

Marc R. Nuwer, et al., IFCN standards for digital recording of clinical EEG, Electroencephalography and clinical Neurophysiology. 1998, pp. 259-261, vol. 106.

Parissa Azadi, Neurofeedback training for symptom reduction in children with dyslexia : multiple case study, Master thesis, 2017, pp. 17-22, NTNU.

Mohammad Ali Nazari et al., The Effectiveness of Neurofeedback Training on EEG Coherence and Neuropsychological Functions in Children With Reading Disability, Clinical EEG and Neuroscience, 2012, pp. 315-322 vol. 43.No. 4.

Marinus H. M. Breteler, et al., Improvements in Spelling after QEEG-based Neurofeedback in Dyslexia: A Randomized Controlled Treatment Study, Appl Psychophysiol Biofeedback, 2009, pp. 5-11, vol. 35, Springer.

Martijn Arns et al., Different Brain Activation Patterns in Dyslexic Children: Evidence From EEG Power and Coherence Patterns for the Double-Deficit Theory of Dyslexia, Journal of Integrative Neuroscience, 2007, pp. 175-190, vol. 6, No. 1.

EMOTIV EPOC X 14 Channel Mobile Brainwear, retrieved from: https://www.emotiv.com/product/emotiv-epoc-x-14-channel-mobile-brainwear.

* cited by examiner

US 11,660,038 B2

SYSTEM BASED ON MULTI-SENSORY LEARNING AND EEG BIOFEEDBACK FOR IMPROVING READING ABILITY

CROSS REFERENCES TO THE RELATED APPLICATIONS

This application is the national phase of International Application No. PCT/TR2017/050572, filed on Nov. 16, 2017, the entire contents of which are incorporated herein by reference.

TECHNICAL FIELD

The present invention relates to a system and method for improving reading ability simultaneously utilizing a distinctive protocol of multi-sensory learning and EEG biofeedback.

BACKGROUND

Dyslexia is a specific learning disability that is neurobiological in origin. It has a prevalence of 10 to 15% of children. It is estimated, 83% of children who have been diagnosed and received treatment continue their academic life without issues. It is characterized by difficulties with accurate and/or fluent word recognition and by poor spelling and decoding abilities. These difficulties typically result from a deficit in the phonological component of language that is often unexpected in relation to other cognitive abilities and the provision of effective classroom instruction. Secondary consequences may include problems in reading comprehension and reduced reading experience that can impede growth of vocabulary and background knowledge (Lyon et al. Ann Dyslexia. 2003 53:1-14).

Dyslexia is probably the most common neurobiological disorder affecting children. Reading problems manifest themselves mainly in the following areas: difficulty in learning to utilize correspondence regularities between graphemes and phonemes poor phonological awareness, i.e., awareness of the sound structure of words, especially phonemic awareness as manifested in the ability to analyze and manipulate sounds within a syllable and poor use of orthographic word reading strategies; and consequently inaccurate and non-fluent word identification. As a result of these difficulties, full alphabetic or phonological reading skills are often not attained (Arns et al. J Integr Neurosci. 2007. 6:175-190).

Electroencephalography (EEG) reveals periodic variations in electrical activity within the brain, which has traditionally been characterized as combinations of four frequency bands or components; which are delta (<4 Hz), theta (4-8 Hz), alpha (8-12 Hz), and beta (12-35 Hz). While the state of consciousness is the primary cause of one frequency being dominant over the other, subtle variations in these components frequently indicate underlying disorders.

The most frequently reported EEG abnormality in children with learning disabilities is an increase in theta relative power according to their age. Several studies have reported higher amounts of delta, and principally theta, and lower amounts of alpha in children with learning disabilities compared to normal children of the same age. An important percentage of children with learning disabilities show EEG patterns that are more typical for younger children, which has been interpreted as a delay of EEG maturation. Other groups of children with learning disabilities show paroxysmal EEG activity (Fernandez et al. Clinical EEG. 2003. 34:145-152).

In biofeedback applications, the user's brain activation is depicted in real-time with the goal of helping the user to gain control over specific aspects of the activity in his/her central nervous system. Hence, the user receives direct feedback about their actual brain activation pattern and consequently can learn to gain voluntary control over neural signals. By watching and listening to real-time multi-media representations of its own activity, the brain can modify its functionality and even its structure. Healthy, age appropriate brain activity is rewarded with visual, auditory or even tactile stimulation. In contrast, undesirable patterns of brain activity are ignored or even penalized (Ninaus et al. "Neurofeedback and serious games." Connolly, T M, Hainey, T., Boyle, E., Baxter, G., Moreno-Ger, P. (eds.) 2013:82-110).

Biofeedback has been used for treating some common conditions and disorders. Sometimes the brain transitions into inappropriate states, resulting in the misdirection of emotions or actions. These inappropriate brain states may lead to a number of conditions and disorders in people including, but not limited to, attention-deficit/hyperactivity disorder (ADHD), migraines, seizures, sleep disorders, premenstrual disorder, extreme stress, anxiety attacks, autism, depression and learning disabilities. It is believed that with the aid of biofeedback, a user can train and control their brain to stop these inappropriate states from manifesting. Among others, US 2010/016753, U.S. Pat. No. 8,082,031, US 2010/094156, US 2016/196765, EP 1 304 073, US 2014/200432 and U.S. Pat. No. 8,239,014 disclose systems and methods for providing biofeedback.

US 2010/016753 discloses a portable neurofeedback system that can be used by an ordinary person, that provides real-time feedback. The neurofeedback system includes sensors for capturing, recording and transmitting brain electrical activity; and a portable device for receiving, processing and displaying in real-time the brain electrical activity, wherein the brain electrical activity is provided visually on the portable device as visual feedback. The portable device includes speakers for implementing auditory feedback based on the recorded brain electrical activity. The portable device further include a vibration feedback motor for implementing vibratory feedback based on the recorded brain electrical activity. The portable device further includes a vibration feedback motor for implementing rumble feedback based on the recorded brain electrical activity. US 2010/016753 further discloses a method for neurotherapy that includes providing a neurofeedback system to a user, wherein the neurofeedback system includes sensors for capturing, recording and transmitting brain electrical activity and a portable device for receiving, processing and displaying in real-time the brain electrical activity; configuring the portable device to select a neurofeedback program, wherein the neurofeedback program is loaded within the portable device; placing the sensors on the user such that the brain electrical activity of the user can be captured, recorded and transmitted to the portable device; executing the neurofeedback program on the portable device, wherein the real-time brain electrical activity of the user is continuously displayed on the portable device as visual feedback and the user is able to control the brain electrical activity such that the visual feedback can be manipulated by the user in real-time; and completing the neurofeedback program.

U.S. Pat. No. 8,082,031 discloses an apparatus for low energy neurofeedback treatment, the apparatus comprising EEG leads for attachment to the patient, an EEG amplifier in signal communication with said EEG leads, the EEG amplifier consisting of means to amplify signal received from the leads attached to the patient. A computer is in signal communication with said EEG amplifier to acquire and display the EEG. A computer and EEG amplifier comprises computational means to determine the dominant frequency in each EEG lead pair. The computer also comprises a user interface for providing a predetermined offset frequency, computation means to calculate a prospective treatment frequency by summing the predetermined offset frequency and the dominant frequency, wherein the calculated prospective treatment frequency is not feedback in an amplified form to the EEG leads. U.S. Pat. No. 8,082,031 also discloses a method for low energy neurofeedback treatment, the method consisting of the steps of providing a EEG amplifier in signal communication with a patient, providing a general purpose computer in signal communication with the EEG amplifier to receiver, analyze and display the patient EEG and to calculate a prospective treatment regimen, acquiring EEG signals from the patient in the EEG amplifier, converting the analog EEG signals to a digital format, determining the dominant frequency of the EEG signals in the general purpose computer, calculating a prospect treatment regimen in the general purpose computer, the step of calculating further comprising the step of providing a frequency offset value, calculating a prospective treatment frequency by summing the dominant frequency and frequency offset value, displaying dominant frequency, frequency offset and prospective treatment frequency on the monitor associated with the general purpose computer.

US 2010/094156 discloses a system of recording brainwaves around the head on a low number of channels relative to a QEEG system. It provides recording from a low number of channels to multiple sensor locations, and also provides a system and method to switch between channels instantly to obtain quality biofeedback. The publication further discloses a system for administration of electroencephalographic (EEG) neurofeedback training which includes a plurality of electrode sensors for placement on the head of a trainee, a switching head box electrically connected to the at least two sensors, an interface device which includes at least two EEG signal amplifiers and is electrically connected to the switching head box, and a computer electrically connected to the interface device and which includes software for generating user-control functions which correspond in real time to EEG signals received by the interface device. The switching head box includes a switch having a first conductor at a first position which connects a first electrode sensor to a first EEG signal amplifier of the interface device, and a second conductor at a second position which connects a second electrode sensor to a second EEG signal amplifier, for transmitting EEG signals from the trainee to the computer. The publication further discloses a program including logic that simultaneously identifies at least two independent BEG brainwave signals received by at least two electrical sensors placed on a head of a trainee undergoing biofeedback training. The program includes logic which executes processing of the EEG brainwave signals and records EEG brainwave data derived from the EEG brainwave signals and logic that detects a predetermined time setting for processing the EEG brainwave signals and executes a prompt, at the conclusion of the predetermined time setting, to advance a switch if additional electrical sensors are to be processed.

US 2016/196765 discloses a computing device connected to sensors executing an application program. While the user interacts with the application program, the sensors detect and measure the user's brain activity and motion. Based on these measurements, the computing device computes an attention score and a motion score for the user. The attention score quantifies the user's level of attention while interacting with the computing program, while the motion score quantifies the amount of user motion or movement (e.g., fidgeting) while interacting with the application program. These scores are then fed into the application program as input parameters in a feedback loop to control the execution of the application program and provide feedback to the user. The publication also discloses a method comprising executing a video game application on a computing device, wherein the video game application generates a virtual environment for display to a user, and objects that are controllable by the user within the virtual environment. While the user interacts with the video game application, the method comprises receiving neurofeedback indicating the user's concentration level while the user is controlling the objects, receiving motion feedback indicating the user's motion while the user is controlling the objects, and while the user is controlling the objects, determining the user's performance on go/no-go tasks generated by the video game application.

EP 1 304 073 discloses a sensor unit recording psycho physiological data from user's individual sensors. A software unit calculates activity data from parameters provided by the sensor which is passed to a function module. These are assembled into group activity data or passed to individual or group related users. The activity data is then represented by display, sound or other forms of stimulation. The software unit and function module form a mental unit configured as, e.g. an Internet server enabling users to log on to obtain a training menu for therapeutic or research purposes.

US 2014/200432 discloses a system for facilitating a subject's functional development including sensing devices configured for sensing mind state signals; sensing devices configured for sensing body state signals; and a set of processing resources configured for generating a mind state indicator/measure, a body state indicator/measure, and a mind-body synergy indicator/measure that corresponds to which each of the subject's mind state and body state are aligned for facilitating the subject's functional development. The system can be configured for concurrently presenting a set of activities involving a model body part; engaging in attempted imitation of the set of activities by way of attempted movement of a body part that is a mirror image of the model body part; presenting an indication of an extent to which each of the mind state and body state are cooperative with respect to performance of the set of activities; and presenting an indication of relaxation.

Finally U.S. Pat. No. 8,239,014 discloses a method of low energy neurofeedback treatment, the method comprising the steps of attaching a plurality of EEG leads to the head of a the patient, acquiring a baseline EEG, calculating the FFT (Fast Fourier Transform) of the acquired baselines for at least 16 time segments, calculating a COV (Covariance) from the FFT for each of the leads, providing a neurofeedback treatment to the patients via the leads, the neurofeedback being provided in the sequence of EEG leads characterized by a higher COV to lower COV.

Therefore, an extensive number of applications can be referred to and currently, popular methods for improving reading ability of people with learning disabilities involve multisensory teaching/learning. Multisensory teaching techniques and strategies stimulate learning by engaging subjects on multiple levels, encouraging them to use some or all of their senses. As an example, the Orton-Gillingham approach is a multisensory instruction, characterized by visual, auditory, and kinesthetic/tactile learning, with an instructional approach that is provided systematically and cumulatively, requiring the mastery and overlearning of information. The Orton-Gillingham instructional program and other programs derived from this original curriculum are still in use today (Ashbaugh. "Multi-Sensory Techniques in Spelling Instruction: An Action Research Study for Students with Dyslexia." 2016).

The present invention aims to provide a system and method for improving reading ability utilizing combinations of multi-sensory learning and EEG biofeedback. By combining these two approaches, a powerful and robust system and method for improving reading ability is presented.

A primary object of the present invention is to provide a system and method for improving reading ability.

Another object of the present invention is to provide an EEG biofeedback protocol specifically designed for learning disabilities.

Another object of the present invention is to provide an EEG biofeedback protocol integrated with multisensory learning.

Another object of the present invention is to provide an EEG biofeedback system suitable for home use and that can work with different EEG signal headsets.

Another object of the present invention is to provide a dedicated user software module/application on portable electronic devices for improving reading ability.

SUMMARY

According to the present invention, a system and method for improving reading ability is proposed, the system relying on a distinctive protocol of multi-sensory learning and EEG biofeedback. The EEG biofeedback protocol is specifically designed for learning disabilities and the EEG biofeedback system integrated with multisensory learning provides a powerful and robust tool for improving reading ability. The EEG biofeedback system is easily usable and does not require theoretical knowledge.

According to a first embodiment of the present invention, a single user software module/application on a portable electronic device for improving reading ability is provided. The single user software may include a multi-sensory application which contains videos, pictures and audition of letters, words, text. Before the training or concurrently with the training, EEG signals are read from a sufficient number of electrodes (1-14) from the user's scalp and these EEG signals are translated to auditory and visual feedback to improve the user's brain performance. If this software is used sufficient number of times, the user's reading speed is increased and the error rate during reading is reduced. The software contains norm data collected from healthy people and people with learning disabilities. This data is used for determining thresholds.

In other words, the threshold values for EEG signals are set with norm data collected from healthy people and people with learning disabilities, therefore, the subject's performance can be statistically compared to that of a large population database (Quantitative Electroencephalograph; qEEG).

BRIEF DESCRIPTION OF THE DRAWINGS

Accompanying drawings are given solely for the purpose of exemplifying an EEG biofeedback system, whose advantages over prior art were outlined above and will be explained in brief hereinafter.

The drawings are not meant to delimit the scope of protection as identified in the Claims, nor should they be referred to alone in an effort to interpret the scope identified in said Claims without recourse to the technical disclosure in the description of the present invention.

DETAILED DESCRIPTION OF THE EMBODIMENTS

Figure 1:
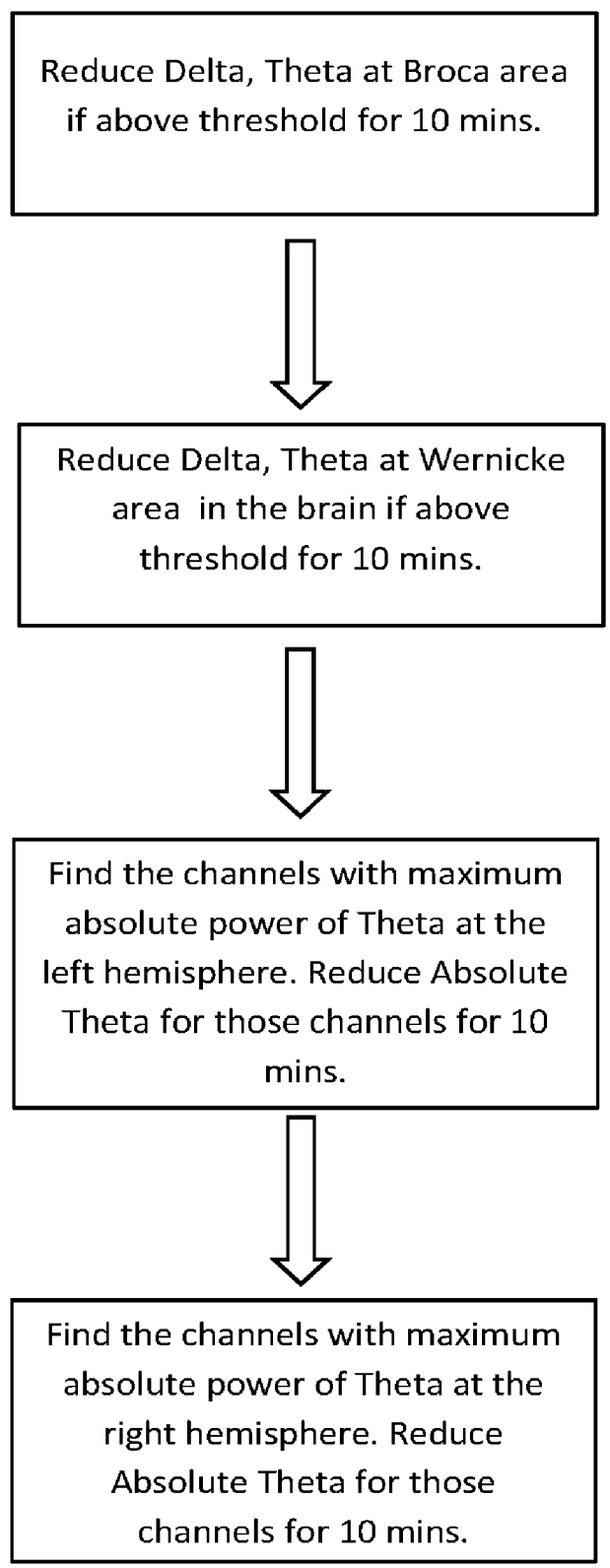
FIG. 1 demonstrates a general flow diagram according to which the EEG biofeedback system of the invention executes various functions.
Figure 2:
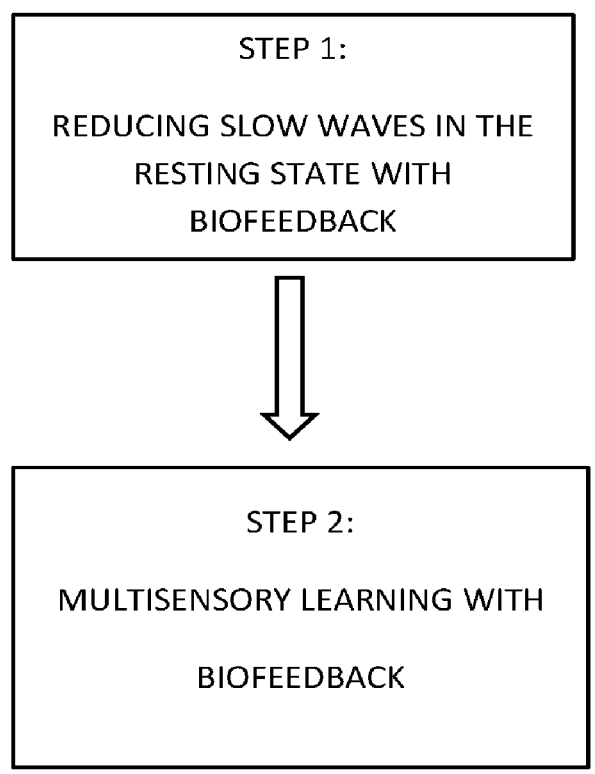
FIG. 2 demonstrates a general flow diagram according to a second optional embodiment of the present invention where the EEG biofeedback system is configured to perform multi-sensory learning tasks simultaneously with biofeedback.
Figure 3:
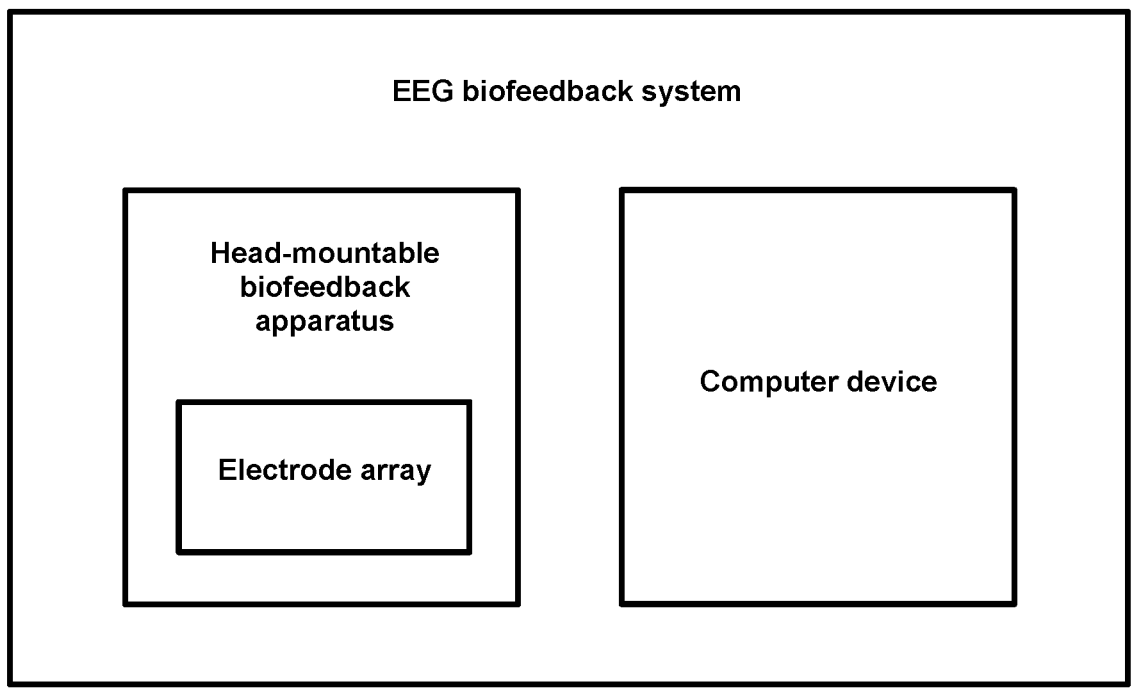
FIG. 3 demonstrates elements of the EEG biofeedback system.

Dyslexia is a specific learning disability that is neurobiological in origin. It has a prevalence of 10 to 15% of children. It is estimated, 83% of children who have been diagnosed and received treatment continue their academic life without issues. It is characterized by difficulties with accurate and/or fluent word recognition and by poor spelling and decoding abilities. There is also reported a connection between learning problems and dementia. Therefore, lifelong and continuous learning is critical to improve cognitive capacity and preserve health.

For the most part, the difficulties in learning to read and write that are typical of dyslexia, are caused by a fundamental problem with speech processing. In the speech processing system, specific roles for Broca's area and Wernicke's area have been suggested: Broca's area being involved in an output code and Wernicke's area (the superior temporal gyrus) in some form of input code. Further evidence, however, shows that Wernicke's area is not only activated by auditory language input, but also by language tasks which do not involve auditory stimulation (Paulesu et al. Brain. 1996. 119:143-157).

The EEG biofeedback system is suitable for use with the International 10-20 system (Klem et al. Electroencephalogr Clin Neurophysiol. 1999. 52:3-6) for electrode placement. More preferably, the EEG biofeedback system utilizes the 10% electrode system, also called the extended 10-20 electrode system, (Nuwer et al. Electroencephalogr Clin Neurophysiol. 1998. 106:259-261) which provides high-resolution EEG measurements. By using 10% electrode system, it is possible to more accurately target Broca's area and Wernicke's area.

Individuals can typically benefit from biofeedback sessions by consciously directing their brainwaves. The biofeedback system can typically make use of a video game setup with visual and audio feedback. For instance an animation with music changing in frequency, volume, and rhythm can allow the subject to respond to generated audiovisual feedback by adapting to a voluntary and better controlled functional state.

The present invention discloses an EEG biofeedback system comprising a biofeedback apparatus in the form of a head-mountable device including an electrode array for measuring bioelectrical signals generated by a cerebral cortex of a user's brain and a computer device receiving and analyzing data collected by said biofeedback apparatus and providing audiovisual feedback to the user such that said EEG biofeedback system is configured to reduce (a) delta and theta waves at Broca area if above threshold for at least 10 minutes, (b) reduce delta and theta waves at Wernicke area in the brain if above threshold for at least 10 minutes, (c) find the channels with maximum absolute power of theta waves at the left hemisphere and reduce absolute theta for those channels for at least 10 minutes, (d) find the channels with maximum absolute power of theta waves at the right hemisphere and reduce absolute theta for those channels for at least 10 minutes.

The biofeedback apparatus in the form of a head-mountable device according to the invention can for instance be an Emotiv EPOC+ headset (trade name) with 16 electrodes (AF3, AF4, F7, F8, F3, F4, FC5, FC6, T7, T8, CMS, DRL, P7, P8, 01 and 02 according to the 10-20 system).

According to a second optional embodiment of the present invention, the EEG biofeedback system is configured to perform multi-sensory learning tasks simultaneously with biofeedback. It is established that parallel execution of (A) multi-sensory learning (through pictures, sound, video) to teach letters, predetermined words/sentences and in general text and (B) simultaneously biofeedback to increase Beta-1, Beta-2 if below threshold is additionally particularly advantageous. It is to be noted the inventors of the present invention have found that when biofeedback is applied during a cognitive task (i.e. during multi-sensory learning), the positive affect is substantially higher than applying biofeedback at the resting state. Therefore, the EEG biofeedback system configured to perform tasks (a) to (d) above during a resting period preferably additionally performs biofeedback during cognitive tasks (multi-sensory learning).

Biofeedback during resting state as described in (a) to (d) followed by biofeedback during cognitively active state is found to be associated with improved treatment achievements such that the speed of reading is measurably increased and the number of errors are substantially reduced.

Preferably, steps (a) to (d) followed by cognitive step biofeedback sessions are repeated at least 20 sessions.

It is to be noted that the EEG biofeedback system is suitable for home use and can work with different EEG signal headsets.

In a nutshell, the present invention proposes an EEG biofeedback system comprising a biofeedback apparatus in the form of a head-mountable device including an electrode array for measuring bioelectrical signals generated by a cerebral cortex of a human brain and a computer device receiving and analyzing data collected by said biofeedback apparatus and providing audiovisual feedback to the user such that said EEG biofeedback system is configured to reduce: (a) delta and theta waves at Broca area if above threshold for at least 10 minutes, (b) reduce delta and theta waves at Wernicke area in the brain if above threshold for at least 10 minutes, (c) find the channels with maximum absolute power of theta waves at the left hemisphere and reduce absolute theta for those channels for at least 10 minutes, (d) find the channels with maximum absolute power of theta waves at the right hemisphere and reduce absolute theta for those channels for at least 10 minutes.

In a further aspect of the present invention, activity of delta and theta waves at Broca area are read by electrodes F3, F7 and FC5 according to International 10-20 system.

In a further aspect of the present invention, activity of delta and theta waves at Wernicke area are read by electrode T7 according to modified combinatorial nomenclature international 10-20 system.

In a further aspect of the present invention, the EEG biofeedback system is additionally configured to perform biofeedback during a cognitively active period induced by a multi-sensory learning process.

In a further aspect of the present invention, the multi-sensory learning process involves use of pictures, sound and video to teach letters, predetermined text.

In a further aspect of the present invention, the EEG biofeedback system is configured to perform biofeedback to increase Beta-1 and/or Beta-2 waves if below threshold In a further aspect of the present invention, the EEG biofeedback system is configured to perform steps (a) to (d) as set forth in the claims followed by cognitively active state biofeedback process as set forth in the claims at least 20 sessions.

What is claimed is:

1. An EEG biofeedback system comprising:
   a head-mountable biofeedback apparatus including an electrode array for measuring bioelectrical signals generated by a cerebral cortex of a user's brain;
   a computer device for receiving and analyzing the bioelectrical signals measured by the head-mountable biofeedback apparatus, and providing an audiovisual feedback to the user; and
   wherein the audiovisual feedback is provided to the user in response to the user consciously directing the brainwaves of the user to:
   (a) reduce delta and theta waves at Broca area in the user's brain,
   (b) reduce delta and theta waves at Wernicke area in the user's brain,
   (c) reduce a maximum absolute power of theta waves measured from a first electrode of the electrode array at a left hemisphere of the user's brain, and
   (d) reduce a maximum absolute power of theta waves measured from a second electrode of the electrode array at a right hemisphere of the user's brain,
   wherein the EEG biofeedback system is configured to perform a multi-sensory learning process simultaneously with the providing of the audiovisual feedback, and
   wherein the multi-sensory learning process includes using pictures, sounds, and videos to teach letters or predetermined texts to the user.

2. The EEG biofeedback system according to claim 1, wherein the delta and theta waves at the Broca area are measured by electrodes F3, F7, and FC5 of the electrode array.

3. The EEG biofeedback system according to claim 1, wherein the delta and theta waves at the Wernicke area are measured by electrode T7 of the electrode array.

4. An EEG biofeedback method performed by an EEG biofeedback system comprising a head-mountable biofeedback apparatus and a computer device, wherein the EEG biofeedback method comprises:
   measuring bioelectrical signals generated by a cerebral cortex of a user's brain by the head-mountable biofeedback apparatus;
   receiving and analyzing, by the computer device, the bioelectrical signals measured by the head-mountable biofeedback apparatus;
   providing, by the computer device, an audiovisual feedback to the user; and
   performing a multi-sensory learning process simultaneously with the providing of the audiovisual feedback, wherein the multi-sensory learning process includes using pictures, sounds, and videos to teach letters or predetermined texts to the user,
   wherein the audiovisual feedback is provided to the user in response to the user consciously directing the brainwaves of the user to:

(a) reduce delta and theta waves at Broca area in the user's brain,
(b) reduce delta and theta waves at Wernicke area in the user's brain,
(c) reduce a maximum absolute power of theta waves measured from a first electrode of an electrode array at a left hemisphere of the user's brain, and
(d) reduce a maximum absolute power of theta waves measured from a second electrode of the electrode array at a right hemisphere of the user's brain.

* * * * *